(12) United States Patent
Sudo

(10) Patent No.: US 10,039,448 B2
(45) Date of Patent: Aug. 7, 2018

(54) OPHTHALMIC APPARATUS

(71) Applicant: CANON KABUSHIKI KAISHA, Tokyo (JP)

(72) Inventor: Takashi Sudo, Inagi (JP)

(73) Assignee: Canon Kabushiki Kaisha, Tokyo (JP)

( * ) Notice: Subject to any disclaimer, the term of this patent is extended or adjusted under 35 U.S.C. 154(b) by 51 days.

(21) Appl. No.: 15/188,224

(22) Filed: Jun. 21, 2016

(65) Prior Publication Data

US 2016/0374552 A1 Dec. 29, 2016

(30) Foreign Application Priority Data

Jun. 23, 2015 (JP) ................................. 2015-125372

(51) Int. Cl.
| | | |
|---|---|---|
| *A61B 3/14* | (2006.01) | |
| *A61B 3/12* | (2006.01) | |
| *A61B 3/10* | (2006.01) | |
| *G02B 27/12* | (2006.01) | |

(52) U.S. Cl.
CPC .......... *A61B 3/1225* (2013.01); *A61B 3/1015* (2013.01); *A61B 3/1025* (2013.01); *G02B 27/126* (2013.01)

(58) Field of Classification Search
CPC .... A61B 3/1225; A61B 3/1015; A61B 3/1025
USPC ........................................ 351/205, 206, 246
See application file for complete search history.

(56) References Cited

U.S. PATENT DOCUMENTS

| | | | | | |
|---|---|---|---|---|---|
| 5,504,543 | A | * | 4/1996 | Ueno ................... | A61B 3/145 351/206 |
| 2010/0110377 | A1 | * | 5/2010 | Maloca ................. | A61B 3/102 351/208 |

FOREIGN PATENT DOCUMENTS

| | | |
|---|---|---|
| JP | 2013-248260 A | 12/2013 |
| JP | 2014-079517 A | 5/2014 |

* cited by examiner

*Primary Examiner* — James Greece
(74) *Attorney, Agent, or Firm* — Carter, Deluca, Farrell & Schmidt, LLP

(57) ABSTRACT

An ophthalmic apparatus capable of suppressing ghost, and securing a necessary amount of working distance even when an eye to be inspected has a diopter on a myopia side, includes: a large area image acquisition unit acquiring a large area image of a fundus of the eye to be inspected at a low resolution based on return light of first measuring light from the fundus; a small area image acquisition unit acquiring a small area image of the fundus at a high resolution based on return light of second measuring light from the fundus; and a dichroic prism combining the first measuring light and the second measuring light, and dividing the return light, in which the large area image acquisition unit includes an optical member having a positive optical power, which is arranged at a position opposite to the eye to be inspected with respect to the dichroic prism.

15 Claims, 4 Drawing Sheets

CONJUGATE POINT OF MYOPIA  -8D  -10D  -12D  -14D

OPHTHALMIC APPARATUS

BACKGROUND OF THE INVENTION

Field of the Invention

The present invention relates to an ophthalmic apparatus, which is configured to acquire an image of a fundus of an eye to be inspected, for example. More specifically, the present invention relates to an ophthalmic apparatus capable of acquiring a small area image of a minute region of the eye to be inspected at a high resolution, and of acquiring a large area image of a larger area of the eye to be inspected at a low resolution.

Description of the Related Art

There has been known an aberration compensation technology in which aberrations of reflected light of light projected on a fundus of an eye to be inspected are sensed by a wavefront sensor arranged at a position conjugate to a pupil of the eye to be inspected, and in which the aberrations are compensated by an aberration compensation device. There has also been performed an investigation in which the aberration compensation technology is utilized to acquire an image of a minute region of the fundus at a high resolution, and in which information on a shape and a density of photoreceptors, a flow of blood cells, and the like is used for diagnosis. Moreover, at the time of acquisition of the image of the minute region, a fundus image acquired of a large area is used to select a region on which the high-resolution image is to be acquired. Therefore, there has been known the structure in which, separately from a fundus image acquisition portion configured to acquire the image of a small region of the fundus at the high resolution, a large area fundus image acquisition portion configured to acquire the image of a large region on the fundus is provided.

In the above-mentioned structure, a dichroic mirror is commonly used to divide light from the fundus into two optical paths leading to the optical system configured to acquire the small area image and the optical system configured to acquire the large area image, which have been described above. In this case, a wavelength of measuring light used in the optical system configured to acquire the small area image is set to be different from a wavelength of measuring light used in the optical system configured to acquire the large area image. Then, the measuring light obtained from each of light sources having different wavelengths of the respective optical systems is irradiated on the fundus, and return light from the fundus is divided by the dichroic mirror (see Japanese Patent Application Laid-Open No. 2014-79517). With this method, acquisition of the small area image and the large area image of the fundus may be realized at the same time.

However, the image acquisition apparatus using the optical systems described in Japanese Patent Application Laid-Open No. 2014-79517 has a problem in that ghost is caused. In order to adapt to a diopter of an individual eye to be inspected, the image acquisition apparatus includes a focusing optical system configured to adjust the diopter. In order to adapt to an eye to be inspected on a myopia side, when an attempt is made to focus the image acquisition apparatus on the fundus, a conjugate point of the fundus is brought closer to the eye side as compared to an emmetropic eye.

Here, in FIG. 8, a correspondence between a diopter and a distance from the eye to the conjugate point of the fundus is illustrated. For example, when a degree of myopia of the eye to be inspected is −12 diopters (D), the conjugate point is located 86 mm (=1,000/12) from the eye. Meanwhile, when the diopter of the eye to be inspected is changed from the myopia side to a hyperopia side, the conjugate point of the fundus is shifted to the side of the light source of the measuring light along with the change.

Therefore, when the structure in which a lens is arranged on the light source side of the conjugate point is adopted as in Japanese Patent Application Laid-Open No. 2014-79517, the return light, that is, the ghost is inevitably caused at a lens surface. Further, when the conjugate point coincides with the lens surface, especially strong ghost is caused. When such ghost enters an avalanche photodiode (APD) sensor, image quality is significantly deteriorated. Moreover, when the ghost enters the wavefront sensor, the sensor malfunctions due to the ghost, and cannot perform appropriate wavefront compensation.

In order to solve the above-mentioned problem, it can be contemplated to avoid causing the ghost by reducing a surface reflectance of the lens. Meanwhile, a reflectance of the fundus, of which the image is to be acquired, is extremely low, and hence an intensity of the light from the fundus becomes lower. To address this problem, the reflectance of the lens surface at least needs to be 0.05% or lower. However, in mass production, stably reducing the reflectance of the lens surface to 0.05% or lower is difficult in terms of forming a thin film on the lens surface, and hence is not practical at present.

It can also be contemplated to avoid ghost by arranging the lens as close to the eye side as possible with respect to the conjugate point of the fundus. However, in that case, a distance (working distance) between the eye to be inspected and the dichroic mirror is reduced. When the working distance is small, there may arise a problem in that the apparatus and the nose interfere with each other, for example.

It can further be contemplated to interchange the arrangement of the dichroic mirror and the lens to obtain the structure in which the lens and the dichroic mirror are arranged in the stated order from the eye side. However, in this structure, the lens is shared for both optical paths of the optical system configured to acquire the small area image and the optical system configured to acquire the large area image. In this case, particularly in the optical system configured to acquire the small area image, the wavefront sensor, which has high sensitivity to ghost, may cause malfunctions, and hence it becomes difficult to acquire the image with high resolution.

SUMMARY OF THE INVENTION

The present invention has been made in view of the above-mentioned circumstances, and therefore has an object to provide an ophthalmic apparatus capable of suppressing ghost, and of securing a necessary amount of working distance even when an eye to be inspected has a diopter on a myopia side.

In order to achieve the above-mentioned object, according to one embodiment of the present invention, there is provided an ophthalmic apparatus, including:

a large area image acquisition unit configured to acquire a large area image of a fundus of an eye to be inspected at a low resolution based on return light of first measuring light from the fundus;

a small area image acquisition unit configured to acquire a small area image of the fundus at a high resolution based on return light of second measuring light from the fundus; and a dichroic prism configured to guide the first measuring light and the second measuring light to the eye to be inspected, and to guide the return light of the first measuring light and the return light of the second measuring light from the eye to be inspected to the large area image acquisition unit and the small area image acquisition unit, respectively, in which the large area image acquisition unit includes an optical member having a positive optical power, which is arranged at a position opposite to the eye to be inspected with respect to the dichroic prism.

According to the present invention, even when an eye to be inspected has a diopter on a myopia side, ghost can be suppressed, and a necessary amount of working distance can be secured.

Further features of the present invention will become apparent from the following description of exemplary embodiments with reference to the attached drawings.

DESCRIPTION OF THE EMBODIMENTS

Now, exemplary embodiments of the present invention are described in detail with reference to the attached drawings. The following embodiments are not intended to limit the present invention defined in the appended claims, and not all combinations of features described in the embodiments are essential to solving means of the present invention.

(First Embodiment)

Figure 1:
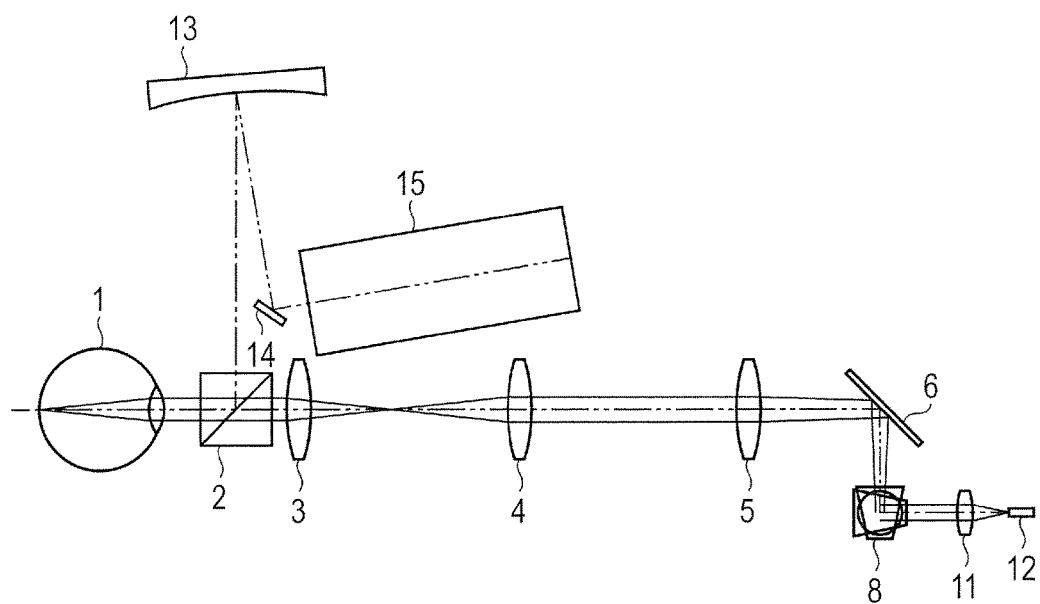
FIG. 1 is a schematic view for schematically illustrating components of an ophthalmic apparatus according to a first embodiment of the present invention, which are arranged in a vertical direction with respect to an eye to be inspected.
Figure 2:
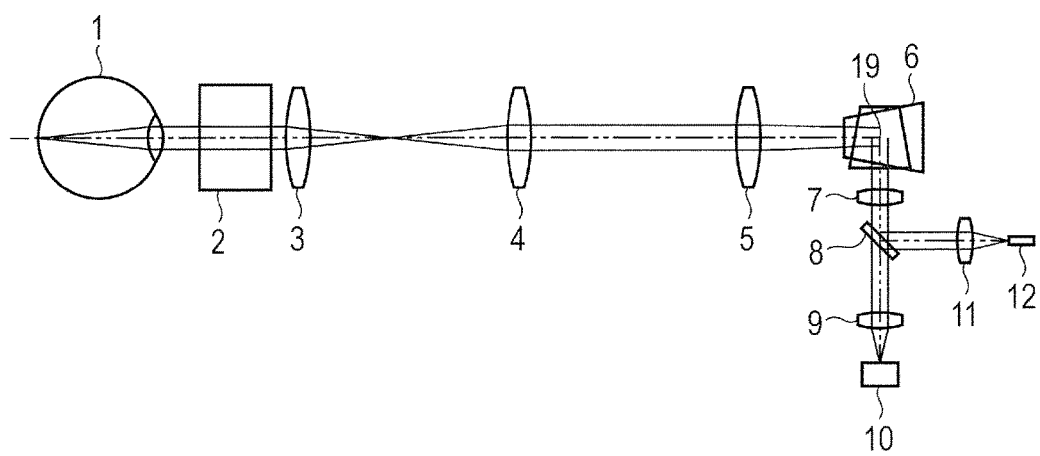
FIG. 2 is a schematic view for schematically illustrating the components of the ophthalmic apparatus according to the first embodiment of the present invention, which are arranged in a horizontal direction with respect to the eye to be inspected.

In each of FIG. 1 and FIG. 2, the schematic structure of an ophthalmic apparatus according to a first embodiment of the present invention is illustrated. FIG. 1 is a schematic view for schematically illustrating components relating to the present invention, which are arranged in a vertical direction with respect to an eye to be inspected 1 (when viewed from the side), and FIG. 2 is a schematic view for schematically illustrating the same components as in FIG. 1, which are arranged in a horizontal direction (when viewed from above).

In the ophthalmic apparatus, in order from in front of the eye to be inspected 1, a dichroic prism 2, an ocular lens 3, a lens 4, a lens 5, a first scanner 6, a second scanner 19, a lens 7, and an optical path dividing mirror 8 are arranged. Moreover, in an optical path divided by transmission by the optical path dividing mirror 8, a lens 9 and a sensor 10 are arranged in the stated order from the mirror, and in an optical path divided by reflection, a lens 11 and a fiber end 12 are arranged in the stated order from the mirror.

The ocular lens 3 has a positive optical power, and the lenses 4, 5, 7, 9, and 11 also have positive optical powers. The first scanner 6 is configured to use a scanning mirror to scan the eye with measuring light in the vertical direction, and the second scanner 19 is configured to use a scanning mirror to scan the eye with measuring light in the horizontal direction. As the sensor 10, an avalanche photodiode (APD) sensor is used. The fiber end 12 indicates an output end portion of a fiber configured to guide laser light emitted from a laser light source (not shown). The laser light corresponds to first measuring light (also referred to as "WF measuring light") in this embodiment. In the present invention, an optical system in which the above-mentioned components are arranged is used as an optical system configured to acquire a large area image of a fundus of the eye to be inspected 1 at a low resolution, or a large area image acquisition unit. The large area image acquisition unit is configured to acquire the large area image of the fundus of the eye to be inspected 1 at the low resolution based on return light of the first measuring light from the fundus.

As illustrated in FIG. 1, in an optical system arranged above the dichroic prism 2, in order from the dichroic prism 2 on an optical path, a spherical mirror 13, a scanning mirror 14, and a small area image acquisition optical system 15 are arranged. The small area image acquisition optical system 15 is configured to function as a small area image acquisition unit in this embodiment, and to acquire a small area image of the fundus at a high resolution based on return light of second measuring light (also referred to as "AO measuring light"), which is to be described later, from the fundus. In other words, the small area image acquisition optical system 15 is arranged on the optical path folded in a direction of reflection on a reflective surface of the dichroic prism 2.

The spherical mirror 13 is arranged above the dichroic prism 2 with respect to the eye to be inspected 1 in the figure, and has a positive optical power. The scanning mirror 14 is configured to scan the eye to be inspected 1 with the measuring light in the vertical direction. The small area image acquisition optical system 15 is a reflecting mirror optical system having a positive optical power, and is formed of a plurality of reflecting mirrors. The use of the plurality of reflecting mirrors is capable of decreasing the influence of the ghost. The small area image acquisition optical system 15 also includes a wavefront aberration measurement unit (not shown) configured to measure a wavefront aberration of the return light of the second measuring light from the fundus, and a wavefront aberration compensation unit (not shown) configured to compensate for the wavefront aberration of the second measuring light or the return light. Detailed optical systems of the small area image acquisition unit and the large area image acquisition unit are publicly known (for example, Japanese Patent Application Laid-Open No. 2013-248260), and hence a description on the detailed structure thereof is omitted.

Next, optical actions of the ophthalmic apparatus according to the first embodiment of the present invention are described. The WF measuring light that has exited the fiber end 12 is converted into substantially parallel light by the lenses 11 and 7 having the positive optical powers, and enters the second scanner 19. A reflective surface of the second scanner 19 is configured to oscillate in a predetermined angle range with 45° being the center and at a predetermined frequency, and to scan the fundus with the WF measuring light in the angle range. The first scanner 6 is configured to oscillate a reflective surface thereof in a direction different from that of the second scanner 19. The WF measuring light enters the reflective surface of the first scanner 6 via the second scanner 19 to scan the fundus of the eye to be inspected vertically and horizontally.

Figure 5:
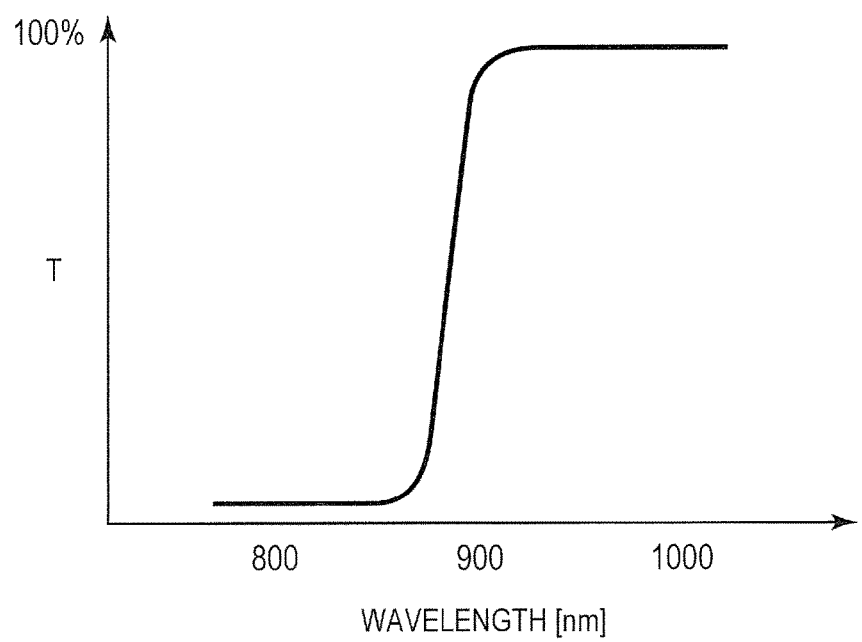
FIG. 5 is a graph for showing membrane characteristics of a dichroic prism used in each of the first embodiment and a second embodiment of the present invention.

The WF measuring light that has exited from those scanners enters the lenses 5 and 4 having the positive optical powers, and is guided to the ocular lens 3 while being collected. The WF measuring light forms an image once between the ocular lens 3 and the lens 4, and then enters the ocular lens 3. The WF measuring light that has entered the ocular lens 3 is converted into substantially parallel light by the lens 3 having the positive optical power, and enters the dichroic prism 2. The dichroic prism 2 has spectral characteristics shown in FIG. 5, and has a transmission characteristic for a wavelength of the light emitted from the fiber end 12. The wavelength of the WF measuring light in this embodiment is 920 nm. In the graph of FIG. 5, the vertical axis indicates a transmittance, and the horizontal axis indicates the wavelength.

The laser light source (not shown) in the small area image acquisition optical system 15 is a laser light source configured to emit the second measuring light having a wavelength that is different from that of the laser light source in the large area image acquisition unit, and is configured to emit light having a wavelength of 840 nm in this embodiment. In other words, the wavelength of the light source of the first measuring light in the above-mentioned large area image acquisition optical system and the wavelength of the light source of the second measuring light in the small area image acquisition optical system 15 are different from each other.

The small area image acquisition optical system 15 is formed of a reflecting optical system to take measures against ghost caused by reflection on a lens surface. The AO measuring light emitted from the small area image acquisition optical system 15 is scanned by the scanning mirror 14, and is reflected to the spherical mirror 13 side. The AO measuring light that has entered the spherical mirror 13 is guided by the dichroic prism 2, and enters the dichroic prism 2 as substantially parallel light. The light that has entered the dichroic prism 2 is reflected by the spectral characteristics shown in FIG. 5, and is guided to the eye to be inspected 1. The dichroic prism 2 has a prism shape, and is configured to guide the first measuring light and the second measuring light to the eye to be inspected, and to divide the return light of the first measuring light and the return light of the second measuring light from the eye to be inspected to the respective optical paths depending on the wavelengths.

Figure 3:
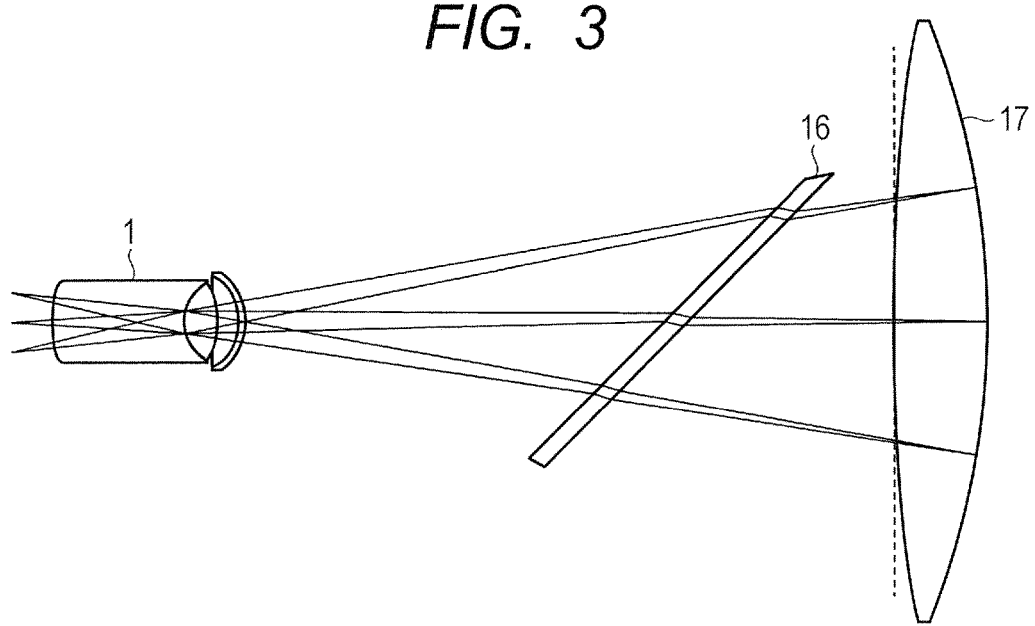
FIG. 3 is a view for illustrating a conjugate position of a fundus with a degree of myopia of −12 diopters in the related-art structure.

Next, principles of the present invention are described. FIG. 3 is a view for illustrating a conjugate position of a fundus with a degree of myopia of −12 diopters in the related-art optical structure. In the related art, as in the structure described in Japanese Patent Application Laid-Open No. 2014-79517, for example, switching between optical paths for acquiring a small area image and a large area image is performed by a dichroic mirror 16. In a case of such optical structure that the dichroic mirror 16 is used to divide the optical paths, ghost is prone to be caused when the eye to be inspected is myopic.

The dotted line portion in FIG. 3 indicates a position conjugate to the fundus (retina) in a case where the degree of myopia is −12 diopters. As in this figure, when the conjugate position of the fundus is in proximity to a surface of an ocular lens 17, the return light from the lens surface directly enters the APD sensor 10, and image quality is deteriorated. As a result, the image of the fundus cannot be acquired at high image quality.

Figure 4:
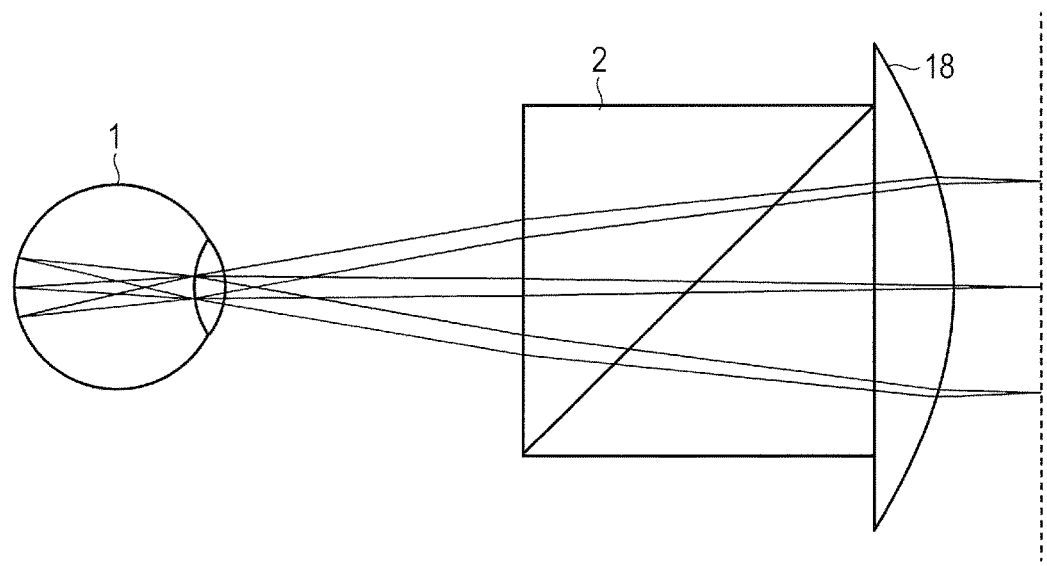
FIG. 4 is a view for illustrating a conjugate position of a fundus with a degree of myopia of −12 diopters in the first embodiment of the present invention.

FIG. 4 is a view for illustrating principles of this embodiment, and a position conjugate to the fundus is illustrated in a manner similar to FIG. 3 for comparison. In this embodiment, the dichroic mirror arranged between the eye to be inspected 1 and an ocular lens 18 is replaced by the dichroic prism 2. The dotted line portion in the figure indicates the position conjugate to the fundus in a case where a degree of myopia is −12 diopters as in FIG. 3. According to this embodiment, the conjugate position may thus be brought away from the ocular lens 18, and hence ghost is less likely to be caused by the reflection from the lens surface.

Moreover, when the eye to be inspected transitions from myopia to hyperopia, the conjugate position is shifted to the light source side. Therefore, in order to reduce ghost for every diopter, the conjugate position of the fundus in the case of myopia needs to be set on the light source side of the ocular lens. In contrast, in this embodiment, an optical path dividing unit between the eye to be inspected and the ocular lens is a prism, and hence a distance from the eye to be inspected to the conjugate position of the fundus may be increased. In this embodiment, the prism used is S-BSM25 (refractive index: 1.65). In this manner, the conjugate position of the fundus for myopia may be brought away from the ocular lens 18, and hence ghost may be reduced.

(Second Embodiment)

Figure 6:
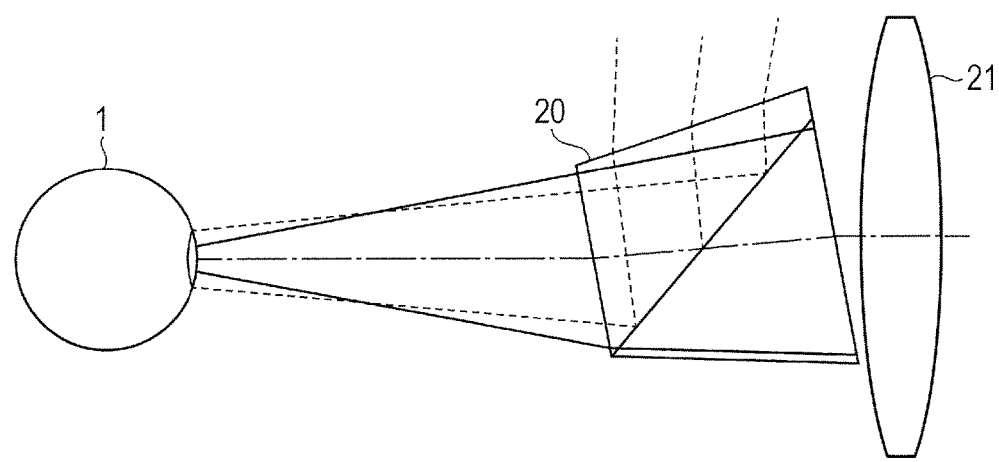
FIG. 6 is a schematic view for schematically illustrating components of an ophthalmic apparatus according to the second embodiment of the present invention, which are arranged from an eye to be inspected to an ocular lens in a vertical direction with respect to the eye to be inspected.

Next, a second embodiment of the present invention is described with reference to FIG. 6. FIG. 6 is a view for schematically illustrating components of an ophthalmic apparatus according to this embodiment, which are arranged from an eye to be inspected 1 to an ocular lens 21, and the other components are similar to those described in the first embodiment. In the first embodiment, the return light from the surface of the ocular lens may be reduced, but light reflected on surfaces (surfaces each of the first measuring light and the second measuring light enters and exits) of the dichroic prism 2 cannot be reduced. Therefore, the second embodiment adopts the structure in which a dichroic prism 20 is decentered, and in which an entrance surface and an exit surface thereof are tilted with respect to an optical axis of the ocular lens 21. At the same time, a tilt angle of the surfaces of the dichroic prism 20 is set larger than the maximum field angle (maximum field angle of the large area image acquisition unit) to prevent reflected light from the surfaces of the dichroic prism 2 from entering the APD sensor 10 for light at any field angle.

Figure 7:
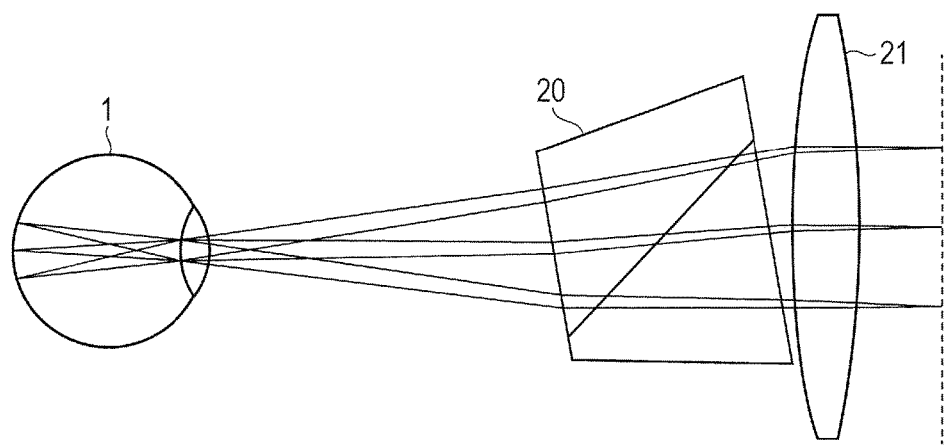
FIG. 7 is a view for illustrating a conjugate position of a fundus with a degree of myopia of −12 diopters according to the second embodiment of the present invention.
Figure 8:
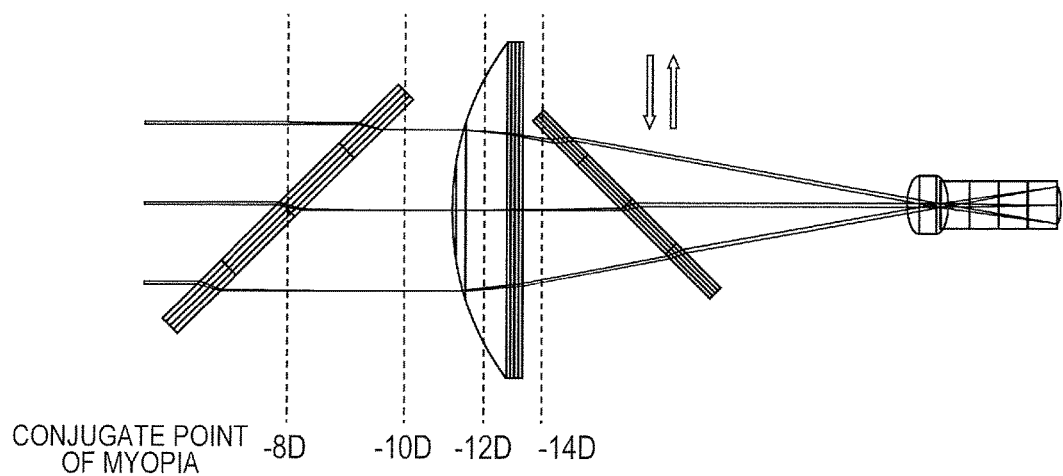
FIG. 8 is a view for illustrating a relationship between a degree of myopia in diopter and the conjugate position of the fundus in the related-art structure.

FIG. 7 is a view for illustrating principles of this embodiment, and a position conjugate to the fundus is illustrated in a manner similar to FIG. 4 for comparison. The dotted line portion in the figure indicates a conjugate position of the fundus in a case where the degree of myopia is −12 diopters. In this embodiment, as illustrated in this figure, the conjugate position of the fundus may be arranged on the light source side away from the ocular lens 21. Therefore, ghost caused by every diopter ranging from myopia to hyperopia may be reduced. Moreover, the reflected light from the output surface of the dichroic prism 20 is prevented from entering the APD sensor 10 with the tilt of the prism surfaces. Therefore, in this embodiment, the ghost reduction effect is even higher than the first embodiment described above.

The first and second embodiments described above have a feature that the refractive index of the dichroic prism is 1.4 or more and 1.7 or less for the following reason. That is, when the refractive index falls below the lower limit value of 1.4, the effect of bringing the conjugate position of the fundus away from the lens is reduced. When the refractive index exceeds the upper limit value of 1.7, membrane characteristics are deteriorated. More specifically, when the refractive index is too high, a critical angle becomes smaller because an adhesive between the dichroic prisms has a refractive index of 1.5, and hence it becomes difficult to obtain desired characteristics.

Moreover, in the first and second embodiments, the eye to be inspected 1, the dichroic prism 2 or the dichroic prism 20, and the ocular lens 3 or the ocular lens 21 are configured to be arranged linearly in the stated order. In other words, the ocular lens 3 or the ocular lens 21, which is an optical member having a positive optical power in the large area image acquisition unit, is arranged at a position opposite to the eye to be inspected 1 with respect to the dichroic prism 2 or the dichroic prism 20.

When the order of the dichroic prism 2 or the dichroic prism 20 and the ocular lens 3 or the ocular lens 21 is interchanged, ghost is caused by the reflection on the surfaces of the ocular lens 3 or the ocular lens 21 in the optical system configured to acquire the small area image, and it becomes difficult to compensate for the aberrations. Therefore, the ocular lens 3 or the ocular lens 21 is not provided between the eye to be inspected 1 and the dichroic prism 2 or the dichroic prism 20.

Now, reasons why the small area image acquisition unit, which is the optical system configured to acquire the image of the small area on the fundus, is arranged above the eye to be inspected, and why the large area image acquisition unit, which is the optical system configured to acquire the image of the large area on the fundus, is arranged substantially on an extension of an axial length of the eye to be inspected are described. The large area image acquisition unit has a large field angle, and hence the ocular lens becomes larger. Therefore, if the large area image acquisition unit is arranged in a direction of folding by the dichroic prism, a working distance cannot be secured. In other words, the structure in which the ocular lens projects on the eye side disadvantageously results.

According to the present invention, there can be provided the ophthalmic apparatus for fundus image acquisition including an aberration compensation device, which is capable of acquiring the small area image and the large area image of the fundus at the same time. In the apparatus, the ghost reduction can be realized, and hence the malfunction during aberration compensation can be reliably avoided, with the result that the image can be acquired stably with the image quality of high resolution. In addition, the working distance from the eye to the image acquisition apparatus can be secured, and hence operability can be improved.

(Other Embodiments)

In the above-mentioned embodiments, a scanning laser ophthalmoscope (SLO) is given as an example to which the present invention is applied, but the present invention may also be applied to an optical coherence tomography (OCT) apparatus, a fundus camera, a perimeter, a tonometer, and other such ophthalmic photographing apparatus, or a combination with a plurality of the ophthalmic photographing apparatus, for example. Alternatively, the present invention may be applied to an apparatus obtained by combining those ophthalmic photographing apparatus.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-125372, filed Jun. 23, 2015, which is hereby incorporated by reference herein in its entirety.

What is claimed is:

1. An ophthalmic apparatus, comprising:
   a large area image acquisition unit configured to acquire a large area image of a fundus of an eye to be inspected at a low resolution based on first return light of first measuring light from the fundus;
   a small area image acquisition unit configured to acquire a small area image of the fundus at a high resolution based on second return light of second measuring light from the fundus; and
   a dichroic prism configured to guide the first measuring light and the second measuring light to a common optical path toward the eye to be inspected, and to separate a return light from the eye to be inspected to the first return light toward the large area image acquisition unit and the second return light toward the small area image acquisition unit,
   wherein the large area image acquisition unit includes an optical member having a positive optical power, which is arranged at a position opposite to the eye to be inspected with respect to the dichroic prism.

2. The ophthalmic apparatus according to claim 1, wherein the eye to be inspected, the dichroic prism, and the optical member having the positive optical power are arranged linearly.

3. The ophthalmic apparatus according to claim 1, wherein the dichroic prism has an entrance surface and an exit surface, which are arranged with a tilt from an optical axis of the optical member having the positive optical power.

4. The ophthalmic apparatus according to claim 1, wherein the dichroic prism has a refractive index of 1.4 or more and 1.7 or less.

5. The ophthalmic apparatus according to claim 1, wherein a wavelength of the first measuring light in the large area image acquisition unit and a wavelength of the second measuring light in the small area image acquisition unit are different from each other.

6. The ophthalmic apparatus according to claim 1, wherein the small area image acquisition unit comprises a reflecting mirror optical system.

7. The ophthalmic apparatus according to claim 1, wherein the small area image acquisition unit includes a wavefront aberration compensation unit configured to compensate for a wavefront aberration of one of the second measuring light and the return light of the second measuring light from the fundus.

8. The ophthalmic apparatus according to claim 1, wherein the small area image acquisition unit is arranged on an optical path in a direction of reflection on a reflective surface of the dichroic prism.

9. An ophthalmic apparatus, comprising:
   a first image acquisition unit configured to acquire a first image of a fundus of an eye to be inspected based on a first return light of first measuring light from the fundus via a first image acquisition optical system, the first image acquisition optical system comprising a refracting optical system;

a second image acquisition unit configured to acquire a second image of the fundus based on a second return light of second measuring light from the fundus via a second image acquisition optical system, the second image acquisition optical system comprising a reflecting optical system, the second image having a size that is smaller than a size of the first image; and a dichroic prism configured to guide the first measuring light and the second measuring light to a common optical path toward the eye to be inspected, and to separate a return light from the eye to be inspected to the first return light of the first measuring light toward the first image acquisition optical system, and the second return light of the second measuring light from the eye to be inspected toward the second image acquisition optical system, respectively, wherein the first image acquisition optical system includes an optical member having a positive optical power, which is arranged in proximity to a surface of the dichroic prism from which the return light exits.

10. The ophthalmic apparatus according to claim 9, wherein the second image acquisition optical system includes a reflecting optical member, which is arranged at a position corresponding to the surface of the dichroic prism from which the return light exits.

11. The ophthalmic apparatus according to claim 9, wherein the first image acquisition optical system is formed of a plurality of lenses.

12. The ophthalmic apparatus according to claim 9, wherein the second image acquisition unit includes a compensation optical system configured to compensate for aberrations of the second return light, and wherein the first image acquisition unit does not include the compensation optical system.

13. The ophthalmic apparatus according to claim 10, wherein the first image acquisition optical system is arranged in a direction in which the first return light is transmitted through a reflective surface of the dichroic prism, and the second image acquisition optical system is arranged in a direction in which the second return light is reflected on the reflective surface.

14. The ophthalmic apparatus according to claim 9, wherein the dichroic prism is arranged so that the surface from which the first return light exits to the first image acquisition optical system is tilted with respect to an optical axis of the first image acquisition optical system.

15. The ophthalmic apparatus according to claim 9, wherein the optical member comprises an optical member configured to shift a conjugate point of the fundus of the eye to be inspected in a direction away from the fundus.

* * * * *